(12) United States Patent
Von Hagen et al.

(10) Patent No.: US 8,143,381 B2
(45) Date of Patent: Mar. 27, 2012

(54) USE OF IONIC LIQUIDS FOR MEMBRANE PROTEIN EXTRACTION

(75) Inventors: Joerg Von Hagen, Pfungstadt (DE); Uwe Michelsen, Weinheim (DE); Maria Wehsling, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 212 days.

(21) Appl. No.: 12/515,117

(22) PCT Filed: Oct. 18, 2007

(86) PCT No.: PCT/EP2007/009010
§ 371 (c)(1),
(2), (4) Date: May 15, 2009

(87) PCT Pub. No.: WO2008/058604
PCT Pub. Date: May 22, 2008

(65) Prior Publication Data
US 2010/0029917 A1    Feb. 4, 2010

(30) Foreign Application Priority Data

Nov. 17, 2006    (DE) .......................... 10 2006 054 329

(51) Int. Cl.
*C07K 1/00* (2006.01)
*C07K 14/00* (2006.01)
(52) U.S. Cl. .......................... 530/422; 530/350; 530/412
(58) Field of Classification Search .................. 530/422, 530/412, 350
See application file for complete search history.

(56) References Cited

U.S. PATENT DOCUMENTS

| 7,470,778 B2 * | 12/2008 | von Hagen et al. ........... 530/412 |
| 2004/0031685 A1 | 2/2004 | Anderson et al. |

FOREIGN PATENT DOCUMENTS

| CN | 1 807 466 | 7/2006 |
| CN | 100362015 | 1/2008 |
| EP | 1 734 047 | 12/2006 |

OTHER PUBLICATIONS

International Search Report for PCT/EP2007/009010 dated Mar. 5, 2008.
Ocean Univ China, "Methods for producing low viscosity algin," Data Supplied from espacenet database—Worldwide, Publication Date: Jul. 26, 2006; English Abstract of CN 1 807 466.
Ruth, M. C. et al., "Analysis of Membrane Proteins from Human Chronic Myelogenouse Leukemia Cells: Comparison fo Extraction Methods for Multidimensional LC-MS/MS," Journal of Proteome Research, 2005, vol. 5, pp. 709-719.

* cited by examiner

*Primary Examiner* — Chih-Min Kam
(74) *Attorney, Agent, or Firm* — Millen, White, Zelano & Branigan, P.C.

(57) ABSTRACT

The present invention relates to the use of ionic liquids or of mixtures comprising at least one ionic liquid and at least one further solvent for the extraction of membrane proteins from biological samples, to methods for the extraction of membrane proteins, to a kit for the extraction of these proteins and to the use thereof.

13 Claims, No Drawings

USE OF IONIC LIQUIDS FOR MEMBRANE PROTEIN EXTRACTION

This application is a U.S. National Phase under §371 of PCT/EP2007/009010, filed Oct. 18, 2007, the disclosure in which is incorporated by reference in its entirety.

The present invention relates to the use of ionic liquids or of mixtures comprising at least one ionic liquid and at least one further solvent for the extraction of membrane proteins from biological samples, to methods for the extraction of membrane proteins, to a kit for the extraction of these proteins and to the use thereof.

The detection or analysis of proteins, very particularly membrane proteins, is of increasing importance in medicine. The majority of the systems investigated in pharmaceutical research comprise membrane proteins. Membrane proteins are of particular importance in a number of biological functions. Thus, many membrane proteins play a major role in the development of diseases, and consequently understanding of their function is of increasing importance in the development of medicaments. Information on the structural property and on the function of these proteins is therefore the basis for understanding of the mechanisms.

Membrane proteins, in particular transmembrane proteins, have hydrophobic regions and are thus anchored in membranes and thus have low solubility in water. In order to facilitate in-vitro analysis of the proteins, membrane proteins are usually solubilised by addition of detergents. However, isolation of membrane proteins with detergents has the serious disadvantage that the native structure of the proteins is denatured by the influence of the detergent. Common detergents are either of an ionic nature, such as, for example, sodium dodecylsulfate (SDS), or of a nonionic nature, such as, for example, Triton-X 100. The use of SDS results in complete denaturing of all proteins and thus also of the membrane proteins, i.e. structural and functional investigations of the membrane proteins are not possible or are only possible to a greatly restricted extent. Triton-X 100 is not capable of effectively extracting membrane proteins, in particular multiple transmembraneous proteins, and consequently the desired investigations cannot take place at all.

The object was therefore to provide methods with the aid of which membrane proteins can be extracted from biological samples in order to be able to analyse them further.

The present invention accordingly relates to the use of at least one ionic liquid or preferably of mixtures comprising at least one ionic liquid and at least one further solvent for the extraction of membrane proteins from biological samples.

In a preferred embodiment, a mixture at least comprising an ionic liquid and a further solvent is employed for the extraction.

In a further preferred embodiment, the further solvent is water. Water-soluble ionic liquids are therefore particularly preferably employed in accordance with the invention.

In a further preferred embodiment, the membrane proteins are proteins which have two or more transmembrane passages.

In a further preferred embodiment, the biological samples are tissue, cells, cell cultures and/or body fluids, bacteria, fungi, viruses or plants.

The present invention also relates to a method for the extraction of membrane proteins from preferably native, biological samples, characterised in that at least one ionic liquid of the general formula $K^+A^-$ or preferably a mixture comprising at least one ionic liquid of the general formula $K^+A^-$ and at least one further solvent is added to a preferably native, biological sample, optionally with mechanical action.

In a preferred embodiment, the biological sample is lysed in advance.

In a particularly preferred embodiment, the lysing of the biological samples is carried out by addition of detergents, surface-active substances or pore formers.

In a preferred embodiment, the mechanical action is effected by shaking or stirring.

In a further preferred embodiment, the anions $A^-$ of the ionic liquid are selected from the group comprising halides, tetrafluoroborate, hexafluorophosphate or imides of the general formula $[N(R_f)_2]^-$ or of the general formula $[N(XR_f)_2]^-$, where $R_f$ denotes partially or fully fluorine-substituted alkyl having 1 to 8 C atoms and X denotes $SO_2$ or CO.

In a further preferred embodiment, the cations $K^+$ of the ionic liquid are selected from the group comprising ammonium, phosphonium, uronium, thiouronium, guanidinium cations or heterocyclic cations.

In a further preferred embodiment, the heterocyclic cations are morpholinium cations or imidazolium cations.

In a further preferred embodiment, the extraction is carried out at temperatures of 4 to 37° C.

In a further preferred embodiment, the concentration of the ionic liquid in the mixture comprising at least one ionic liquid and at least one further solvent is between 0.02 and 5% by weight.

In a further preferred embodiment, the ionic liquid is selected from N-(3-hydroxypropyl)-N-methylmorpholinium bistrifluoromethysulfonylimide, 4-(2-methoxyethyl)-4-methylmorpholinium bromide, 4-methyl-4-propylmorpholinium bromide, 4-(2-ethoxyethyl)-4-methylmorpholinium bromide, 4-(3-hydroxypropyl)-4-methylmorpholinium bromide, 4-(2-hydroxyethyl)-4-methylmorpholinium bromide, 4-(3-methoxypropyl)-4-methylmorpholinium bromide, 4-butyl-4-propylmorpholinium bromide, trihexyl(tetradecyl)-phosphonium tetrafluoroborate, 1-decyl-3-methylimidazolium bromide, 1-dodecyl-3-methylimidazolium chloride, 3-methyl-1-octadecylimidazolium hexafluorophosphate or mixtures thereof.

The present invention also relates to a kit for the extraction of membrane proteins by the method according to the invention comprising at least one ionic liquid or preferably mixtures comprising at least one ionic liquid and at least one further solvent and at least one lysing agent selected from the group of the detergents, surface-active substances and/or pore formers.

The present invention also relates to the use of a kit according to the invention for the extraction of membrane proteins from biological samples.

The crux of the present invention is that the method according to the invention and the kit according to the invention are suitable for extracting membrane proteins, in particular multipass membrane proteins, gently and as far as possible with retention of their structure. It is known to the person skilled in the art that, in particular in the case of multipass membrane proteins, function-retaining extraction from the membrane is virtually impossible since the 3D structure of the protein inevitably changes after extraction from the membrane if the transmembrane domains are removed from the hydrophobic environment of the membrane. With respect to the extraction according to the invention of multipass membrane proteins, the term "native" therefore means that, although the extracted membrane proteins are generally not extracted with retention of their function, they are, however, extracted gently and as far as possible with retention of their structure. For example, the extraction according to the invention enables mass-spectrometric and immunological measurement, in particular, of the transmembrane domains of the proteins. Using conventional methods, such as, for example, extraction with Triton-X100, Nonidet P40 or other detergents which are used as standard, this is not possible in a comparable manner in relation to the protein yield and retention of function of the proteins to be investigated.

In the case of membrane proteins which are only anchored in the membrane with a part which is irrelevant for their function or activity, such as, for example, GPI anchor proteins, "native" extraction according to the invention means that the protein can be extracted substantially with retention of its structure and activity. For example, corresponding activity measurements can be carried out in this case for detection of the protein.

Native samples are samples in which the membrane proteins to be extracted are still substantially in their native conformation, i.e. in the conformation necessary for their natural function, or samples in which the membrane proteins still exhibit activity.

The extraction of membrane proteins in accordance with the present invention can be carried out from all biological samples known to the person skilled in the art. The biological samples are preferably tissue, such as, for example, biopsies and histological preparations, cells, cell cultures and/or cell-containing body fluids, such as, for example, blood, urine, liquor or saliva, and bacteria, plants and fungi. Membrane proteins from membrane-containing cell compartments can also be extracted in accordance with the invention. The extraction of proteins from tissues and cell cultures allows, in particular, the detection of specific proteins, for example for the detection of proteins which indicate the presence of diseases. The method according to the invention is therefore also particularly advantageous for pathologically interesting tissue samples.

The method according to the invention is particularly suitable for transmembrane proteins and very particularly for multipass membrane proteins, i.e. proteins which have two or more transmembrane passages, in particular multihelical transmembrane proteins, such as, for example, heptahelical transmembrane proteins. The class of heptahelical transmembrane proteins currently includes about 250 known proteins. The transmembrane proteins can be divided into the following sub-classes:

Class A rhodopsins, hormone proteins, (rhod)opsin, olfactory, prostanoids, nucleotide analogues, cannabinoid, platelet activating factor, gonadotropin-releasing hormones, thyrotropin-releasing hormones and secretagogue, melatonin, viral proteins, lysosphingolipid & LPA (EDG), leukotriene B4 receptors, Class A orphan and others, Class B secretins, for example calcitonin, corticotropin releasing factor, gastric inhibitory peptide, glucagon, growth hormone-releasing hormone, parathyroid hormone, PACAP, secretin, vasoactive intestinal polypeptide, diuretic hormone, EMR1, latrophilin, brain-specific angiogenesis inhibitor (BAI), methuselah-like proteins (MTH), cadherin EGF LAG (CELSR), very large G-protein coupled receptors Class C metabotropic glutamate/pheromone, for example metabotropic glutamate, calcium-sensing like, putative pheromone receptors, GABA-B, orphan GPRC5, orphan GPCR6, bride of sevenless proteins (BOSS), taste receptors (T1R), Class D fungal pheromone, for example fungal pheromone A-factor like (STE2,STE3), fungal pheromone B like (BAR,BBR,RCB,PRA), fungal pheromone M- and P-factor, Class E cAMP receptors, frizzled/lsmoothened family, frizzled, smoothened and in the following non-GPCR families: Class Z archaeal/bacterial/fungal opsins.

Ionic liquids or liquid salts are ionic species which consist of an organic cation and a generally inorganic anion. They do not contain any neutral molecules and usually have melting points below 373 K.

The area of ionic liquids is currently being researched intensively since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten— neue Lösungen für die Übergangsmetallkatalyse" [Ionic Liquids— Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

The ionic liquids to be employed in accordance with the invention are preferably miscible with water, in particular if they are employed, in accordance with a preferred embodiment of the present invention, in a mixture comprising at least one ionic liquid and at least one further solvent. The further solvent is typically water or preferably aqueous buffer systems. It is also possible for smaller amounts of one or more water-soluble organic solvents to be added to the solvent.

The present invention likewise relates to a method for the extraction of membrane proteins from biological samples, in which at least one ionic liquid of the general formula $K^+A^-$ or a mixture comprising at least one ionic liquid of the general formula $K^+A^-$ and at least one further solvent is added to a biological sample, optionally with mechanical action.

In the simplest embodiment of the present invention, at least one ionic liquid of the general formula $K^+A^-$ or a mixture comprising at least one ionic liquid of the general formula $K^+A^-$ and at least one further solvent is added to the biological sample. The said method is preferably carried out with mechanical action, for example by shaking or stirring. In this way, the extraction of the membrane proteins is accelerated and the yield of extracted proteins is improved.

In a further embodiment of the method according to the invention, the biological sample can firstly be lysed, i.e. the cellular basic structure has been destroyed before application of the methods according to the invention. This pretreatment can be carried out in all ways known to the person skilled in the art, for example by manual homogenisation, mechanical shaking. In particular, the lysing of the biological samples can also be carried out by addition of detergents, surface-active substances and pore formers known to the person skilled in the art. The prior lysing of the sample further improves the result of the extraction with respect to the yield of membrane proteins obtained. Thus, the membrane proteins remain in the membrane, the membranes or membrane fragments during lysing, but can be separated off from the other cell constituents in a simple manner. The lysis is preferably carried out with digitonin.

The lysis can also be carried out simultaneously with the extraction, but more complex protein mixtures are then obtained.

In general, all ionic liquids of the general formula $K^+A^-$ known to the person skilled in the art, in particular those which are miscible with water, are suitable in the methods according to the invention.

The anion A⁻ of the ionic liquid is preferably selected from the group comprising halides, tetrafluoroborate, hexafluorophosphate or imides of the general formula [N(R$_f$)$_2$]⁻ or of the general formula [N(XR$_f$)$_2$]⁻, where R$_f$ denotes partially or fully fluorine-substituted alkyl having 1 to 8 C atoms and X denotes SO$_2$ or CO. The halide anions here can be selected from chloride, bromide and iodide anions, preferably from chloride and bromide anions. The anions A⁻ of the ionic liquid are preferably halide anions, in particular bromide anions, or imides of the general formula [N(XR$_f$)$_2$]⁻, where R$_f$ denotes partially or fully fluorine-substituted alkyl having 1 to 8 C atoms and X denotes SO$_2$. R$_f$ is preferably trifluoromethyl, pentafluoroethyl, nonafluorobutyl, in particular trifluoromethyl. Ionic liquids comprising the particularly preferred bromide or [(CF$_3$SO$_2$)$_2$N]⁻ anions are particularly suitable for the extraction of membrane proteins in the methods according to the invention.

There are no restrictions per se with respect to the choice of the cation K⁺ of the ionic liquid. However, preference is given to organic cations, particularly preferably ammonium, phosphonium, uronium, thiouronium, guanidinium cations or heterocyclic cations.

Ammonium cations can be described, for example, by the formula (1)

$$[NR_4]^+ \quad (1),$$

where
R in each case, independently of one another, denotes
H, where all substituents R cannot simultaneously be H,
OR', NR'$_2$, with the proviso that a maximum of one substituent R in formula (1) is OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms,
which may be substituted by alkyl groups having 1-6 C atoms,
where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N⁺R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated C$_1$- to C$_6$-alkyl, C$_3$- to C$_7$-cycloalkyl, unsubstituted or substituted phenyl and X may be =halogen.

Phosphonium cations can be described, for example, by the formula (2)

$$[PR^2_4]^+ \quad (2),$$

where
R² in each case, independently of one another, denotes
H, OR' or NR'$_2$
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R² may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R² which are not in the α-position may be replaced by atoms and/or atom groups selected from the group —O—, —S—, —S(O)—, —SO$_2$—, —SO$_2$O—, —C(O)—, —C(O)O—, —N⁺R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

However, cations of the formulae (1) and (2) in which all four or three substituents R and R² are fully substituted by halogens are excluded, for example the tris(trifluoromethyl)methylammonium cation, the tetra(trifluoromethyl)ammonium cation or the tetra(nonafluorobutyl)ammonium cation.

Uronium cations can be described, for example, by the formula (3)

$$[(R^3R^4N)-C(=OR^5)(NR^6R^7)]^+ \quad (3),$$

and thiouronium cations by the formula (4), $$[(R^3R^4N)-C(=SR^5)(NR^6R^7)]^+ \quad (4),$$

where
R³ to R⁷ each, independently of one another, denotes hydrogen, where hydrogen is excluded for R⁵,
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents R³ to R⁷ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R³ to R⁷ which are not in the α-position may be replaced by atoms and/or atom groups selected from the group —O—, —S—, —S(O)—, —SO$_2$—, —SO$_2$O—, —C(O)—, —C(O)O—, —N⁺R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

Guanidinium cations can be described by the formula (5)

$$[C(NR^8R^9)(NR^{10}R^{11})(NR^{12}R^{13})]^+ \quad (5),$$

where
R⁸ to R¹³ each, independently of one another, denotes hydrogen, —CN, NR'$_2$, —OR'
straight-chain or branched alkyl having 1 to 20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more of the substituents R⁸ to R¹³ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R⁸ to R¹³ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R' where R'=H, non-, partially or perfluorinated C$_1$- to C$_6$-alkyl, C$_3$- to C$_7$-cycloalkyl, unsubstituted or substituted phenyl and X=halogen.

In addition, it is possible to employ cations of the general formula (6)

$$[HetN]^+ \quad (6),$$

where
HetN$^+$ denotes a heterocyclic cation selected from the group

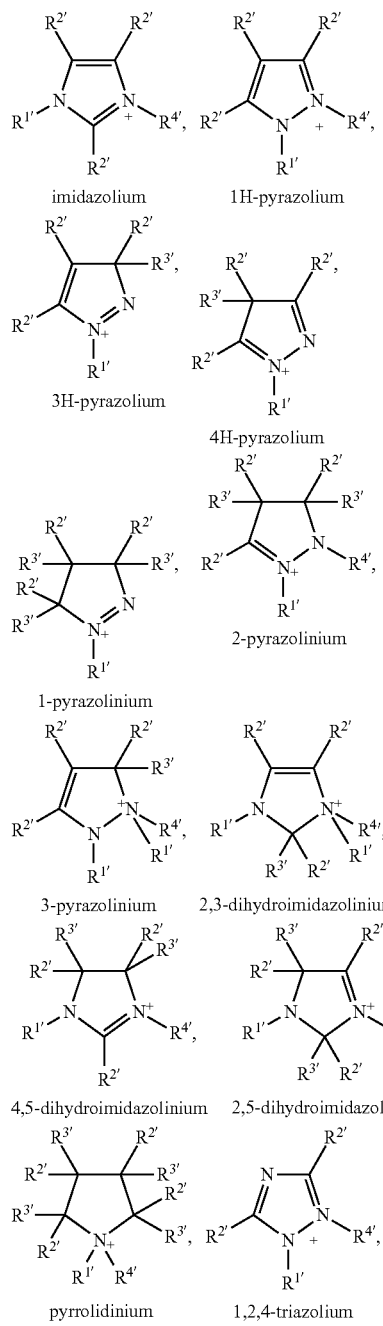

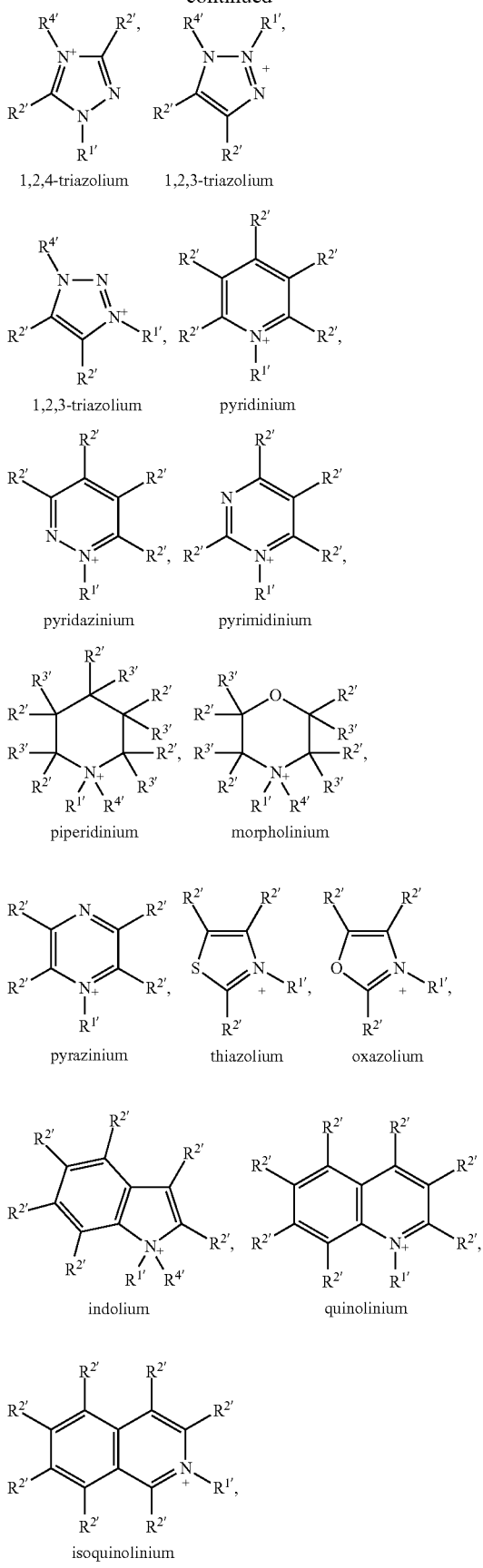

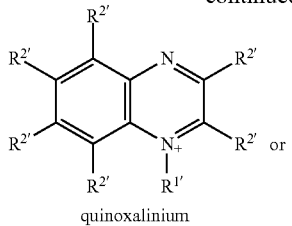

quinoxalinium

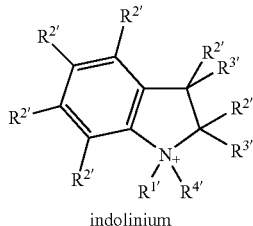

indolinium where the substituents

R$^{1\prime}$ to R$^{4\prime}$ each, independently of one another, denote hydrogen, —CN, —OR', —NR'$_2$, —P(O)R'$_2$, —P(O)(OR')$_2$, —P(O)(NR'$_2$)$_2$, —C(O)R', —C(O)OR', straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-C$_1$-C$_6$-alkyl or aryl-C$_1$-C$_6$-alkyl, where the substituents R$^{1\prime}$, R$^{2\prime}$, R$^{3\prime}$ and/or R$^{4\prime}$ together may also form a ring system, where one or more substituents R$^{1\prime}$ to R$^{4\prime}$ may be partially or fully substituted by halogens, in particular —F and/or —Cl, or —OH, —OR', —CN, —C(O)OH, —C(O)NR'$_2$, —SO$_2$NR'$_2$, —C(O)X, —SO$_2$OH, —SO$_2$X, —NO$_2$, but where R$^{1\prime}$ and R$^{4\prime}$ cannot simultaneously be fully substituted by halogens, and where, in the substituents R$^{1\prime}$ to R$^{4\prime}$, one or two non-adjacent carbon atoms which are not bonded to the heteroatom may be replaced by atoms and/or atom groups selected from the —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

For the purposes of the present invention, fully unsaturated substituents are also taken to mean aromatic substituents.

In accordance with the invention, suitable substituents R and R$^2$ to R$^{13}$ of the compounds of the formulae (1) to (5), besides hydrogen, are preferably: C$_1$- to C$_{20}$-, in particular C$_1$- to C$_{14}$-alkyl groups, and saturated or unsaturated, i.e. also aromatic, C$_3$- to C$_7$-cycloalkyl groups, which may be substituted by C$_1$- to C$_6$-alkyl groups, in particular phenyl.

The substituents R and R$^2$ in the compounds of the formula (1) or (2) may be identical or different here. The substituents R and R$^2$ are preferably different.

The substituents R and R$^2$ are particularly preferably methyl, ethyl, isopropyl, propyl, butyl, sec-butyl, tert-butyl, pentyl, hexyl, octyl, decyl or tetradecyl.

Up to four substituents of the guanidinium cation [C(NR$^8$R$^9$)(NR$^{10}$R$^{11}$)(NR$^{12}$R$^{13}$)]$^+$ may also be bonded in pairs in such a way that mono-, bi- or polycyclic cations are formed.

Without restricting generality, examples of such guanidinium cations are:

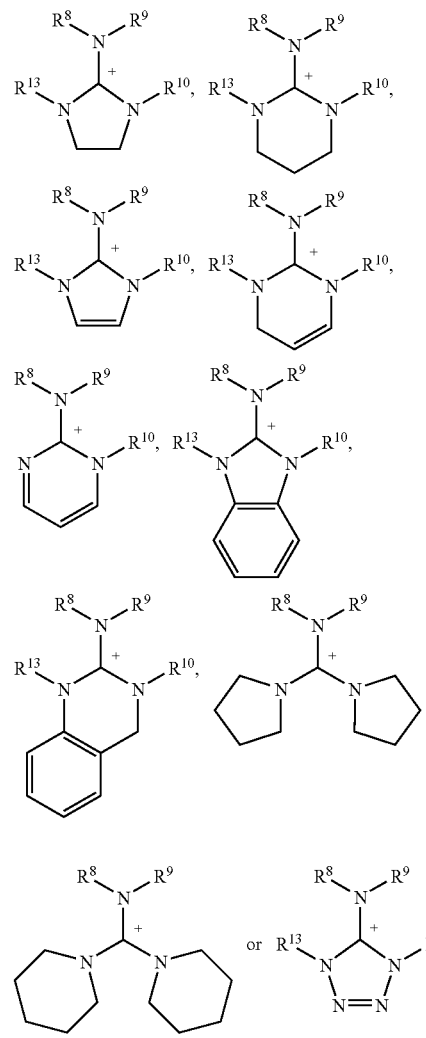

where the substituents R$^8$ to R$^{10}$ and R$^{13}$ can have a meaning or particularly preferred meaning indicated above.

If desired, the carbocyclic or heterocyclic rings of the guanidinium cations indicated above may also be substituted by C$_1$- to C$_6$-alkyl, C$_1$- to C$_6$-alkenyl, NO$_2$, F, Cl, Br, I, OH, C$_1$-C$_6$-alkoxy, SCF$_3$, SO$_2$CF$_3$, COOH, SO$_2$NR'$_2$, SO$_2$X' or SO$_3$H, where X and R' have a meaning indicated above, substituted or unsubstituted phenyl or an unsubstituted or substituted heterocycle.

Up to four substituents of the uronium cation [(R$^3$R$^4$N)—C(=OR$^5$)(NR$^6$R$^7$)]$^+$ or thiouronium cation [(R$^3$R$^4$N)—C(=SR$^5$)(NR$^6$R$^7$)]$^+$ may also be bonded in pairs in such a way that mono-, bi- or polycyclic cations are formed.

Without restricting generality, examples of such cations are indicated below, where Y=O or S:

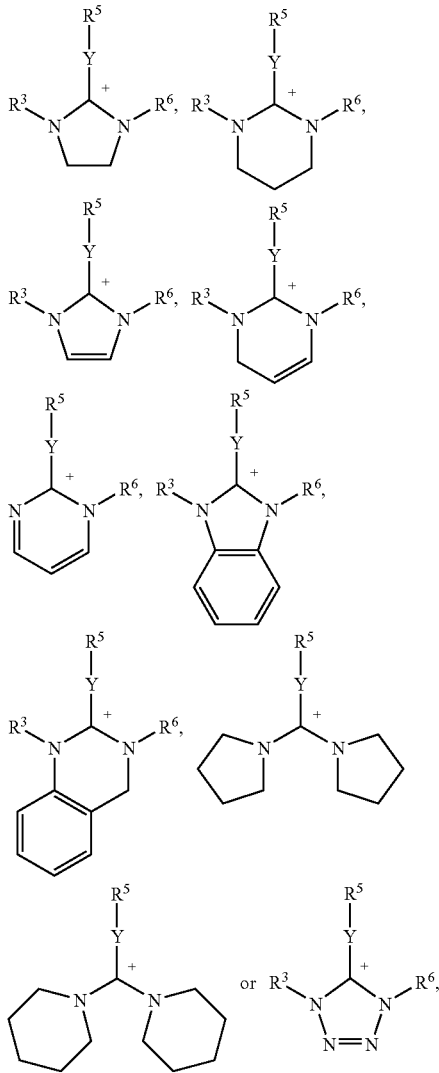

where the substituents $R^3$, $R^5$ and $R^6$ can have a meaning or particularly preferred meaning indicated above.

If desired, the carbocyclic or heterocyclic rings of the cations indicated above may also be substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2NR'_2$, $SO_2X$ or $SO_3H$ or substituted or unsubstituted phenyl or an unsubstituted or substituted heterocycle, where X and R' have a meaning indicated above.

The substituents $R^3$ to $R^{13}$ are each, independently of one another, preferably a straight-chain or branched alkyl group having 1 to 10 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (3) to (5) may be identical or different. $R^3$ to $R^{13}$ are particularly preferably each, independently of one another, methyl, ethyl, n-propyl, isopropyl, n-butyl, tert-butyl, sec-butyl, phenyl or cyclohexyl, very particularly preferably methyl, ethyl, n-propyl, isopropyl or n-butyl.

In accordance with the invention, suitable substituents $R^{1'}$ to $R^{4'}$ of compounds of the formula (6), besides hydrogen, are preferably: $C_1$- to $C_{20}$, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, tert-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular hydrogen, methyl, ethyl, isopropyl, propyl, butyl, sec-butyl, tert-butyl, cyclohexyl, phenyl or benzyl. $R^{2'}$ is particularly preferably hydrogen, methyl, ethyl, isopropyl, propyl, butyl or sec-butyl. $R^{2'}$ and $R^{3'}$ are very particularly preferably hydrogen.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$; preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —CN, —C(O)OH, —C(O)NR'$_2$, —SO$_2$NR'$_2$, —C(O)X, —SO$_2$OH, —SO$_2$X, —NO$_2$.

In the substituents $R^1$, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O, —P(O)(NR'$_2$)NR'—, —PR'$_2$=N— or —P(O)R'— where R'=non-, partially or perfluorinated $C_1$- to $C_6$-alkyl, $C_3$- to $C_7$-cycloalkyl, un-substituted or substituted phenyl.

Without restricting generality, examples of substituents R, $R^2$ to $R^{13}$ and $R^{1'}$ to $R^{4'}$ modified in this way are:

—$OCH_3$, —$OCH(CH_3)_2$, —$CH_2OCH_3$, —$CH_2$—$CH_2$—O—$CH_3$, —$C_2H_4OCH(CH_3)_2$, —$C_2H_4C_2H_5$, —$C_2H_4SCH(CH_3)_2$, —$S(O)CH_3$, —$SO_2CH_3$, —$SO_2C_6H_5$, —$SO_2C_3H_7$, —$SO_2CH(CH_3)_2$, —$SO_2CH_2CF_3$, —$CH_2SO_2CH_3$, —O—$C_4H_8$—O—$C_4H_9$, —$CF_3$, —$C_2F_5$, —$C_3F_7$, —$C_4F_9$, —$C(CF_3)_3$, —$CF_2SO_2CF_3$, —$C_2F_4N(C_2F_5)C_2F_5$, —$CHF_2$, —$CH_2CF_3$, —$C_2F_2H_3$, —$C_3H_6$, —$CH_2C_3F_7$, —$C(CFH_2)_3$, —$CH_2C(O)OH$, —$CH_2C_6H_5$, —$C(O)C_6H_5$ or $P(O)(C_2H_5)_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' denotes F, Cl or Br and R" denotes a non-, partially or perfluorinated $C_1$- to $C_6$-alkyl or $C_3$- to $C_7$-cycloalkyl as defined for R', for example o-, m- or p-methylphenyl, o-, m- or pethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-,2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, $NO_2$, F, Cl, Br, I, OH, $C_1$-$C_6$-alkoxy, $SCF_3$, $SO_2CF_3$, COOH, $SO_2X'$, $SO_2NR''_2$ or $SO_3H$, where X' and R" have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-,3-, 4-, 5-, 6- or 7-benzopyrazolyl, 2-, 4-, 5-, 6- or 7-benzoxazolyl, 3-, 4-, 5-,6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-,7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl, pyridinylhexyl, where the heterocyclic radicals described above may furthermore be linked to the alkylene chain in this way.

HetN$^+$ is preferably

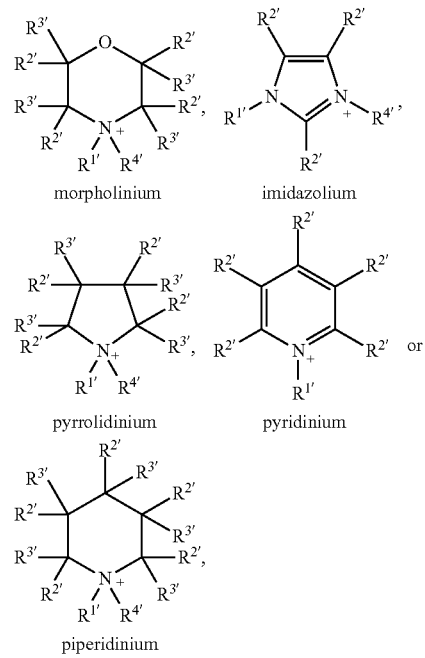

where the substituents $R^{1'}$ to $R^{4'}$ each, independently of one another, have a meaning described above. Morpholinium and imidazolium cations are particularly preferred in the present invention, where $R^{1'}$ to $R^{4'}$ in the said cations denote, in particular, in each case independently of one another, hydrogen, straight-chain or branched alkyl having 1-20 C atoms, where one or more substituents $R^{1'}$ to $R^{4'}$ may be partially substituted by —OH or —OR', where $R^{1'}$=non-, partially or perfluorinated $C_1$- to $C_6$-alkyl, $C_3$- to $C_7$-cycloalkyl, unsubstituted or substituted phenyl.

The cations of the ionic liquid according to the invention are preferably ammonium, phosphonium, imidazolium or morpholinium cations.

Very particularly preferred substituents R, $R^2$, $R^{1'}$ to $R^{4'}$ of the preferred ammonium, phosphonium, imidazolium or morpholinium cations are selected from methyl, ethyl, propyl, butyl, hexyl, decyl, dodecyl, octadecyl, ethoxyethyl, methoxyethyl, hydroxyethyl or hydroxypropyl groups.

Morpholinium trifluoromethylsulfonylimides or morpholinium bromides, phosphonium tetrafluoroborates, imidazolium chlorides, bromides or hexafluorophosphates are very particularly preferably employed for extraction in the methods according to the invention, where N-(3-hydroxypropyl) N-methylmorpholinium bistrifluoromethysulfonylimide, 4-(2-methoxyethyl)-4-methylmorpholinium bromide, 4-methyl-4-propyl-morpholinium bromide, 4-(2-ethoxyethyl)-4-methylmorpholinium bromide, 4-(3-hydroxypropyl)-4-methylmorpholinium bromide, 4-(2-hydroxyethyl)-4-methylmorpholinium bromide, 4-(3-methoxypropyl)-4-methylmorpholinium bromide, 4-butyl-4-propylmorpholinium bromide, trihexyl(tetradecyl)-phosphonium tetrafluoroborate, 1-decyl-3-methylimidazolium bromide, 1-dodecyl-3-methylimidazolium chloride, 3-methyl-1- octadecylimidazolium hexafluorophosphate or mixtures thereof give particularly good results in the methods according to the invention.

In a preferred embodiment of the present invention, mixtures comprising at least one ionic liquid and at least one further solvent are employed for the extraction of membrane proteins from biological samples. In these cases, the concentration of the ionic liquid in the mixture comprising at least one ionic liquid and at least one further solvent is typically 0.02 to 5% by weight, preferably 0.1 to 1% by weight, based on the mixture. Suitable further solvents are mentioned above, preferably water or aqueous buffer systems. Suitable buffers are all buffer systems which produce physiological conditions, i.e. do not denature proteins. Examples are PIPES, HEPES, phosphate buffers and Tris-based buffers In the methods mentioned, the ionic liquids or mixtures comprising at least one ionic liquid and at least one further solvent may comprise additional additives and assistants. Corresponding additives and assistants are known to the person skilled in the art and include, for example, detergents, surface-active substances, pore formers and biological or physiological buffer systems, mineral salts and inhibitors (for example protease inhibitors).

The methods according to the invention can be carried out at temperatures above 0° C., typically between 0 and 95° C. If, in particular, high protein yields are to be achieved and the retention of activity or structure are secondary, the extraction can be carried out at high temperatures (above 37° C.). Extractions of this type can be utilised particularly well for Western blot analyses The extraction according to the invention is preferably carried out at 0 to 37° C., particularly preferably between 0 and 8° C., in particular between 0 and 4° C. At the preferred temperatures, improved extraction in a relatively short time and the retention of the protein activity of the protein is observed. For gentle extraction, in particular of relatively sensitive membrane proteins, it is advisable to carry out the method according to the invention at relatively low temperatures within the stated temperature range, taking into account a longer extraction time necessary for this purpose.

Typical extraction times are between 30 minutes and 16 hours. If active proteins are to be extracted, the pH of the extraction solution (solvent and ionic liquid) should preferably be about pH 7.4, otherwise extraction solutions having pH values between 2 and 10 can also be employed.

The proteins extracted in accordance with the invention can be employed, for example, for mass-spectrometric investigations directly or after gelelectrophoretic separation, for Western blot analyses or activity assays. For some applications, such as, for example, mass-spectrometric determination, the ionic liquid must be removed in advance from the protein extract obtained. This can be carried out, for example, by in-gel digestion by methods known to the person skilled in the art.

The methods according to the invention are suitable for the extraction of membrane proteins from biological samples with retention of the cellular basic structure of the samples, i.e. the structure of the membrane proteins is retained as far as possible. In this way, entire membrane complexes, which can only be isolated with difficulty or not at all using conventional methods, can also be isolated. In general, the membrane proteins obtained can be detected using suitable antibodies The method according to the invention opens up for the first time the possibility of extracting hydrophobic membrane proteins, in particular multipass membrane proteins, in an aqueous system using water-soluble ionic liquids as mild extractants. In this way, gentle extraction is combined with a very simple method procedure. Since an aqueous medium is already used for the extraction, the extract can be investigated directly in a very wide variety of analytical methods without the solvent being exchanged in advance.

The extracts obtained with the aid of the methods according to the invention comprise membrane proteins and are likewise a subject-matter of the present invention. They are suitable for use in all types of protein analysis known to the person skilled in the art, for example electrophoresis (for example gel electrophoresis, in particular also 2-dimensional gel electrophoresis), immunochemical detection methods (for example Western blot analysis, ELISA, RIA), protein arrays (for example planar and bead-based systems), mass spectrometry (for example Maldi, Esi and Seldi) and all chromatographic separation methods, in particular biochromatographic separation methods (IEX, SEC, HIC, affinity chromatography and hydrophobic interaction chromatography).

The present invention likewise relates to a kit for the extraction of membrane proteins using a method according to the invention described above, comprising at least one ionic liquid or mixtures comprising at least one ionic liquid and at least one further solvent. The kit according to the invention may comprise one or more ionic liquids. If the kit comprises a plurality of ionic liquids, these may be separate or together in the form of a mixture. The above-mentioned and particularly preferred ionic liquids are preferably present in the kit.

The kit according to the invention enables the user to extract membrane proteins from biological samples in a simple manner.

The present invention likewise relates to the use of the kits according to the invention for the extraction of membrane proteins, in particular multiple transmembraneous proteins, from biological samples.

Even without further comments, it is assumed that a person skilled in the art will be able to utilise the above description in the broadest scope. The preferred embodiments and examples should therefore merely be regarded as descriptive disclosure which is absolutely not limiting in any way.

EXAMPLES

Human MDA MB 468 breast cancer cells are cultivated in RPMI 1640 medium (2.000 mg/l of D-glucose, 110 mg/l of sodium pyruvate, non-essential amino acids, no L-glutamine, Gibco) to a confluence of 50% in commercially available T75 cell-culture bottles under 5% of $CO_2$ at 37° C. The adherent cells are harvested by means of a cell scraper in Tris-buffered sodium chloride solution (TBS) and protease inhibitors (Calbiochem Protease Inhibitor Cocktail III). The membrane proteins are isolated after liberation of the cytoplasmatic protein fraction by means of pore formers (extraction buffer I) in the 2nd extraction step. Fraction 1 represents the soluble protein fraction, principally of the cytoplasmatic proteins. The fraction after extraction by means of ionic liquid in aqueous buffer solution (extraction buffer II) is the membrane protein fraction. 2% solutions of the ionic liquid are incubated for 30 minutes at 37° C. with gentle shaking. After extraction, the sample are centrifuged for 15 minutes at 16000×g at room temperature. The supernatant (extracted membrane protein fraction) is subsequently employed with commercially available sample application buffer for sodium dodecylsulfate polyacrylamide gel electrophoresis (SDSPAGE). The samples are separated on 10% BIS-tris polyacrylamide (PAA) gels (Novex, Invitrogen). The samples are subsequently transferred to PVDF membranes in accordance with the principle of the "semi-dry Western blot" method. The membranes are subsequently incubated with the following first antibodies:

a) anti-EGFR rabbit antibody (Sc03, Santa Cruz dilution 1:100) as reference of a dimeric receptor molecule,
b) anti-frizzled 4 antibody (R&D Systems MAB 194, diluted 1:500) as reference of a seven-transmembrane-passing protein (7-TM). c) As second reference protein, cadherin EGF-lag seven-transmembrane-passing receptor-3 (CELSR3) antibody is used (Acris).
d) As second antibody for detection, an anti-rabbit-POD antibody from General Electrics (GE) diluted 1:5000 is employed) or an anti-rat-POD anti-body from Pierce in a dilution of 1:5000 is used.

The chemiluminescence detection is carried out by means of a commercially available ECL Western blotting detection kit from GE (#RPN 2106).

The Western blot shows the retention of the native structure of the membrane proteins extracted with the ionic liquid.
TBS: 50 mM Tris
150 mM NaCl
pH 7.4
Extraction Buffer I:
　300 m sucrose
　15 mM NaCl
　10 mM Pipes (piperazine-1,4-bis(2-ethanesulfonic acid))
　0.5 mM EDTA
　0.01875% of digitonin
　pH 7.4
Extraction Buffer II:
　300 mM sucrose
　15 mM NaCl
　10 mM Pipes (piperazine-1,4-bis(2-ethanesulfonic acid))
　0.5 mM EDTA
　2% by weight of N-(3-hydroxypropyl)-N-methylmorpholinium bis(trifluoromethylsulfonyl)imide or 1-dodecyl-3-methylimidazolium chloride
　pH 7.4

We claim:

1. A method for extracting a membrane protein from a biological sample comprising
　contacting said sample with a water-miscible ionic liquid which is N-(3-hydroxypropyl)-N-methylmorpholinium bistrifluoromethysulfonyl imide, 4-(2-methoxyethyl)-4-methylmorpholinium bromide, 4-methyl-4-propylmorpholinium bromide, 4-(2-ethoxyethyl)-4-methylmorpholinium bromide, 4-(3-hydroxypropyl)-4-methylmorpholinium bromide, 4-(2-hydroxyethyl)-4-methylmorpholinium bromide, 4-(3-methoxypropy)-4-methylmorpholinium bromide, 4-butyl-4-propylmorpholinium bromide, trihexyl(tetradecyl) phosphonium tetrafluoroborate, 1-decyl-3-methylimidazolium bromide, 1-dodecyl-3-methylimidazolium chloride, 3-methyl-1-octadecylimidazolium hexafluorophosphate, or a mixture thereof
　or a mixture comprising said water-miscible ionic liquid and at least one further solvent; and
　extracting said membrane protein, optionally with mechanical action.

2. The method according to claim 1, comprising employing a mixture comprising a water-miscible ionic liquid and a further solvent.

3. The method according to claim 2, wherein the further solvent is water.

4. The method according to claim 3, wherein the membrane protein comprises two or more transmembrane passages.

5. The method according to claim 3, wherein the biological sample is a tissue, a cell, a cell culture sample, a body fluid, a bacteria, a fungus, a virus, or a plant.

6. The method according to claim 3, wherein the biological sample is lysed in advance.

7. The method according to claim 3, comprising adding a detergent, a surface-active substance or a pore former for the lysis of said biological sample.

8. The method according to claim 3, wherein the mechanical action is effected by shaking or stirring.

9. The method according to claim 3, wherein the extraction is carried out at temperatures of 4 to 37° C.

10. The method according to claim 3, wherein the concentration of the ionic liquid in the mixture comprising at least one ionic liquid and at least one further solvent is 0.02 to 5% by weight.

11. A method for the extraction of a membrane protein from a biological sample, comprising
　contacting said biological sample with at least one water-miscible ionic liquid which is N-(3-hydroxypropyl)-N-methylmorpholinium bistrifluoromethysulfonylimide, 4-(2-methoxyethyl)-4-methylmorpholinium bromide, 4-methyl-4-propylmorpholinium bromide, 4-(2-ethoxyethyl)-4-methylmorpholinium bromide, 4-(3-hydroxypropyl)-4-methylmorpholinium bromide, 4-(2-hydroxyethyl)-4-methylmorpholinium bromide, 4-(3-methoxypropyl)-4-methylmorpholinium bromide, 4-butyl-4-propylmorpholinium bromide, trihexyl(tetradecyl) phosphonium tetrafluoroborate, 1-decyl-3-methylimidazolium bromide, 1-dodecy1-3-methylimidazolium chloride, 3-methyl-1-octadecylimidazolium hexafluorophosphate, or a mixture thereof;
　or with a mixture comprising said water-miscible ionic liquid and at least one further solvent; and
　extracting said membrane protein with mechanical action.

12. A kit comprising
　at least one ionic liquid or a mixture comprising said ionic liquid which is N-(3-hydroxypropyl)-N-methylmorpholinium bistrifluoromethysulfonylimide, 4-(2-methoxyethyl)-4-methylmorpholinium bromide, 4-methyl-4-propylmorpholinium bromide, 4-(2-ethoxyethyl)-4-methylmorpholinium bromide, 4-(3-hydroxypropyl)-4-methylmorpholinium bromide, 4-(2-hydroxyethyl)-4-methylmorpholinium bromide, 4-(3-methoxypropyl)-4-methylmorpholinium bromide, 4-butyl-4-propylmorpholinium bromide, trihexyl(tetradecyl) phosphonium tetrafluoroborate, 1-decyl-3-methylimidazolium bromide, 1-dodecy1-3-methylimidazolium chloride, 3-methyl-1-octadecylimidazolium hexafluorophosphate, or a mixture thereof;
　and at least one further solvent and
　at least one lysing agent which is a detergent, a surface-active substance or a pore former.

13. A method for the extraction of a membrane protein from a biological sample comprising contacting said biological sample with the kit according to claim 12; and
　extracting said membrane protein, optionally with mechanical action.

* * * * *